United States Patent
Wang et al.

(10) Patent No.: US 9,029,612 B2
(45) Date of Patent: May 12, 2015

(54) PROCESS FOR PRODUCING PHENOL

(75) Inventors: Kun Wang, Bridgewater, NJ (US); Jihad M. Dakka, Whitehouse Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/110,797

(22) PCT Filed: Dec. 15, 2011

(86) PCT No.: PCT/US2011/065058
§ 371 (c)(1),
(2), (4) Date: Dec. 18, 2013

(87) PCT Pub. No.: WO2012/145029
PCT Pub. Date: Oct. 26, 2012

(65) Prior Publication Data
US 2014/0296581 A1  Oct. 2, 2014

Related U.S. Application Data

(60) Provisional application No. 61/476,893, filed on Apr. 19, 2011, provisional application No. 61/502,979, filed on Jun. 30, 2011.

(51) Int. Cl.
| | |
|---|---|
| C07C 37/50 | (2006.01) |
| C07C 37/08 | (2006.01) |
| C07C 45/53 | (2006.01) |
| C07C 407/00 | (2006.01) |
| C07C 51/31 | (2006.01) |
| B01J 29/08 | (2006.01) |
| B01J 29/90 | (2006.01) |
| B01J 31/02 | (2006.01) |

(52) U.S. Cl.
CPC ............. *C07C 37/50* (2013.01); *B01J 29/08* (2013.01); *B01J 29/90* (2013.01); *B01J 31/0244* (2013.01); *C07C 37/08* (2013.01); *C07C 45/53* (2013.01); *C07C 407/00* (2013.01); *C07C 51/31* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 4,439,409 A | 3/1984 | Puppe et al. | |
| 4,826,667 A | 5/1989 | Zones et al. | |
| 4,870,217 A | 9/1989 | Knifton | |
| 4,954,325 A | 9/1990 | Rubin et al. | |
| 5,236,575 A | 8/1993 | Bennett et al. | |
| 5,250,277 A | 10/1993 | Kresge et al. | |
| 5,362,697 A | 11/1994 | Fung et al. | |
| 6,014,018 A | 1/2000 | Wu et al. | |
| 6,037,513 A | 3/2000 | Chang et al. | |
| 6,049,018 A | 4/2000 | Calabro et al. | |
| 6,077,498 A | 6/2000 | Diaz Cabañas et al. | |
| 6,756,030 B1 | 6/2004 | Rohde et al. | |

FOREIGN PATENT DOCUMENTS

| | | | |
|---|---|---|---|
| EP | 0 293 032 | 11/1988 | |
| JP | 2007099745 A * | 4/2007 | ............ C07C 27/00 |
| JP | 2007099746 A * | 4/2007 | ............ C07C 27/00 |
| WO | WO 97/17290 | 5/1997 | |
| WO | WO 2009/025939 | 2/2009 | |
| WO | WO 2009/058527 | 5/2009 | |
| WO | WO 2009/131769 A1 * | 10/2009 | ............ C07C 2/74 |
| WO | WO 2010/042261 A1 * | 4/2010 | ............ C07C 37/08 |
| WO | WO 2010/098916 | 9/2010 | |
| WO | WO 2011/001244 A1 * | 1/2011 | ............ C07C 2/66 |
| WO | WO 2011/031374 | 3/2011 | |
| WO | WO 2011/041801 | 4/2011 | |
| WO | WO 2012/145028 | 10/2012 | |
| WO | WO 2012/145030 | 10/2012 | |
| WO | WO 2012/145031 | 10/2012 | |
| WO | WO 2012/145032 | 10/2012 | |

OTHER PUBLICATIONS

Meier et al., "*Framework type data FAU zeolites*", Atlas of zeolites structure types, Jan. 1, 2001, XP55007150, Retrieved from the Internet: URL:http://izasc.ethz.ch/fmi/xsl/IZA-SC/Atlas_pdf/FAU.pdf, retrieved on Sep. 14, 2011.

Ishii et al., "*Recent progress in aerobic oxidation of hydrocarbons by N-hydroxyimides*", ScienceDirect, Catalysis Today, 117 (2006), pp. 105-113.

\* cited by examiner

*Primary Examiner* — Brian J Davis

(57) ABSTRACT

In a process for producing phenol, cyclohexylbenzene is contacted with oxygen in the presence of an oxidation catalyst comprising a cyclic imide under oxidation conditions effective to produce a product comprising cyclohexylbenzene hydroperoxide and unreacted cyclic imide catalyst. At least a portion of the product is contacted with a cleavage catalyst under conditions effective to convert at least a portion of the cyclohexylbenzene hydroperoxide into a second product comprising further unreacted cyclic imide catalyst, phenol, and cyclohexanone. A portion of the further unreacted cyclic imide catalyst may then be removed from the second product and optionally recycled back to the oxidation step.

22 Claims, 3 Drawing Sheets

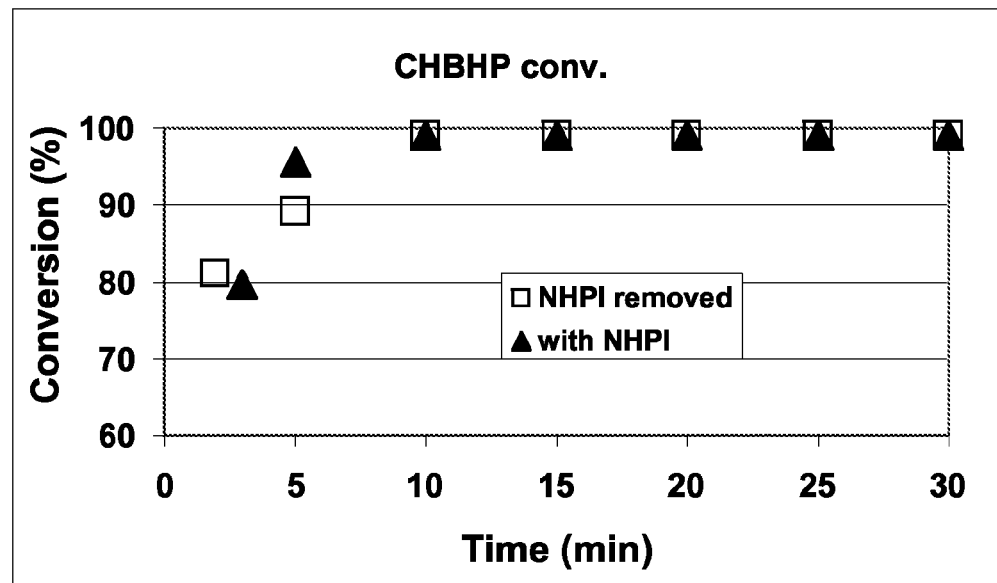
Figure 3. CHBHP Conversion vs. Batch Time
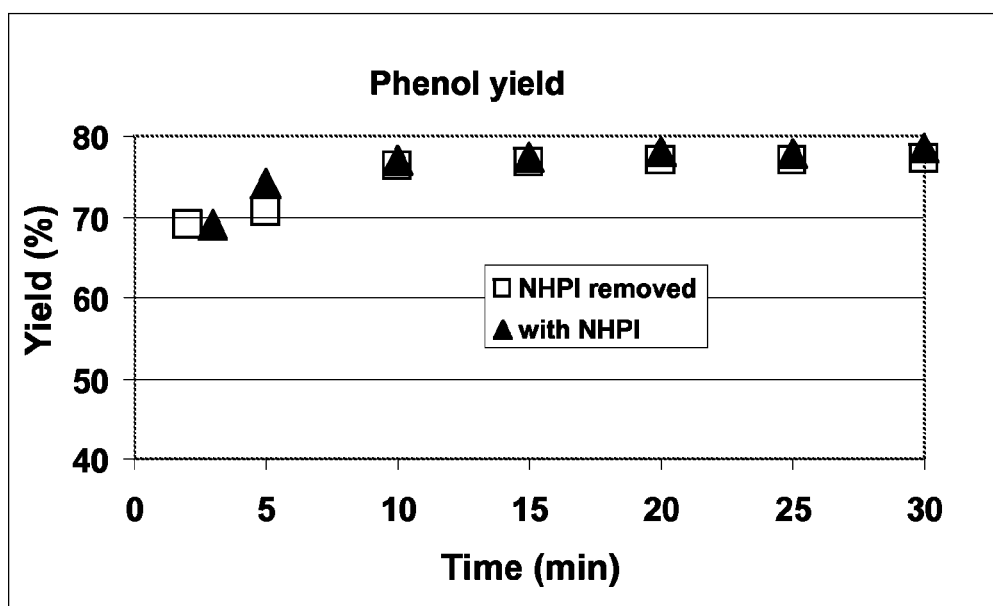
Figure 4. Phenol Yield vs. Batch Time

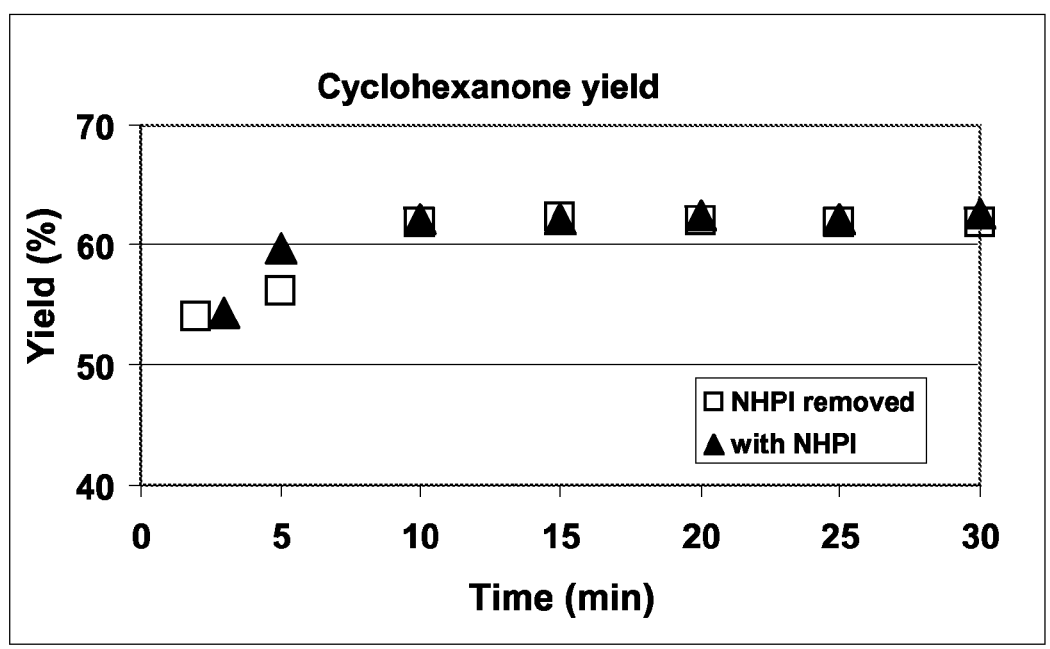
Figure 5. Cyclohexanone Yield vs. Batch time

PROCESS FOR PRODUCING PHENOL

PRIORITY CLAIM TO RELATED APPLICATIONS

This application is a National Stage Application of International Application No. PCT/US2011/065058 filed Dec. 15, 2011, which claims priority to U.S. Provisional Application Ser. No. 61/476,893 filed Apr. 19, 2011, and U.S. Provisional Application Ser. No. 61/502,979 filed Jun. 30, 2011, the disclosures of which are fully incorporated herein by their reference.

CROSS REFERENCE TO RELATED PATENT APPLICATIONS

This application is related to U.S. application Ser. No. 13/143,975 filed Jan. 25, 2010, now allowed; U.S. Provisional Application Ser. No. 61/476,893 filed Apr. 19, 2011; U.S. Provisional Application Ser. No. 61/502,985 filed Jun. 30, 2011; U.S. Provisional Application No. 61/509,258 filed Jul. 19, 2011; and International Patent Cooperation Treaty Application No. PCT/US2011/065063, filed Dec. 15, 2011.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide into equimolar amounts of phenol and acetone, a co-product.

It is also known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product.

There are, however, a number of problems associated with producing phenol via cyclohexylbenzene rather than the cumene-based Hock process. Firstly, oxidation of cyclohexylbenzene to cyclohexylbenzene hydroperoxide is much more difficult than oxidation of cumene and requires elevated temperatures and the use of a catalyst, generally a cyclic imide, such as N-hydroxyphthalimide (NHPI), to achieve acceptable rates of conversion. Additionally, it was generally thought that the cyclic imide catalysts needed to be removed from the oxidation products prior to the cleavage step because they may cause problems in downstream separation processes and affect the quality of the final products.

For example, PCT Patent Publication WO2010/042261 discloses that unreacted cyclic imide catalyst can act as a poison to the downstream cleavage catalyst (e.g., mixed metal oxide). Thus, it will normally be desirable to treat the effluent from the oxidation process to reduce the level of unreacted cyclic imide prior to passage of the effluent to the cleavage step. Generally, the effluent is treated so as to reduce the level of the imide in the organic phase to less than 100 ppm, such as less than 50 ppm, for example less than 10 ppm, by weight of the organic phase.

Moreover, PCT Patent Publication WO2010/098916 also discloses that it will normally be desirable to treat the effluent stream from the oxidation process to remove at least part of the cyclic imide of the first catalyst prior to passage of the effluent stream to the cleavage of the hydroperoxide. In a preferred embodiment, the cyclic imide is removed in a separate vessel that is downstream of the oxidation reactor and upstream of the cleavage reactor. PCT Publication Nos. WO2009/025939; WO 2009/058527; and WO2011/041801 also disclose methods for removing cyclic imide catalysts prior to cleavage reactions.

According to the present invention, it has now been found that the presence of cyclic imide oxidation catalyst in the cleavage feed does not affect selectivity in the cleavage reaction when using certain cleavage catalysts (e.g., sulfuric acid and/or solid acids). This discovery eliminates the need to remove the cyclic imide prior to the cleavage step, resulting in the savings of both capital and operating costs.

SUMMARY

Accordingly, the invention resides in one aspect in a process for producing phenol, the process comprising:
(a) contacting cyclohexylbenzene with an oxygen-containing compound in the presence of an oxidation catalyst comprising a cyclic imide under oxidation conditions effective to produce a first product comprising cyclohexylbenzene hydroperoxide and unreacted cyclic imide catalyst;
(b) contacting at least a portion of the first product with a cleavage catalyst, which is conveniently sulfuric acid and/or solid acids such as acidic molecular sieves, under conditions effective to convert at least a portion of the cyclohexylbenzene hydroperoxide in said first product into a second product comprising further unreacted cyclic imide catalyst, phenol and cyclohexanone, wherein less than 50 wt % of the unreacted cyclic imide catalyst is removed from the first product prior to the contacting step (b), the wt % based upon the weight of the first product; and
(c) removing at least a portion of the further unreacted cyclic imide catalyst from the second product.

Conveniently, less than 30 wt %, or less than 10 wt %, or less than 1 wt %, of the unreacted cyclic imide catalyst is removed from the first product prior to the contacting step (b), based upon the weight of the first product.

Conveniently, the conditions in step (b) include a temperature of about 20° C. to about 200° C. and a pressure of about 100 kPa to about 2000 kPa.

In one embodiment, said contacting step (b) is conducted in at least a first reactor and a second reactor connected in series.

Conveniently, the first reactor is operated at a temperature of about 20° C. to about 120° C. and a pressure of about 100 kPa to about 500 kPa, and the second reactor is operated at a temperature of about 40° C. to about 180° C. and a pressure of about 100 kPa to about 1000 kPa.

In another embodiment, said contacting step (b) is conducted in at least one of a plurality of reactors connected in parallel. Conveniently, the cleavage catalyst is regenerated in a first reactor during operation of the contacting step (b) in a second reactor.

In one embodiment, said contacting step (b) is at least partly conducted in a continuous stirred tank reactor (CSTR). Conveniently, the cleavage catalyst is continuously or periodically withdrawn downstream of the contacting (b) and regenerated. Typically, the regenerated catalyst is returned to the contacting (b). Conveniently, the cleavage catalyst is continuously or periodically added to the contacting (b) to maintain conversion.

In another embodiment, said contacting step (b) is at least partly conducted in a fixed bed reactor.

Conveniently, at least a portion of the cyclic imide catalyst is desorbed from said acidic molecular sieve and recycled to said contacting (a).

In yet a further aspect, the invention resides in a process for producing phenol, the process comprising:
 (a) hydroalkylating benzene with hydrogen in the presence of a hydroalkylation catalyst under conditions effective to produce a hydroalkylation reaction product comprising cyclohexylbenzene;
 (b) separating cyclohexylbenzene from said hydroalkylation reaction product;
 (c) contacting at least a portion of said cyclohexylbenzene from said separating step (b) with an oxygen-containing compound in the presence of an oxidation catalyst comprising a cyclic imide under oxidation conditions effective to produce a first product comprising cyclohexylbenzene hydroperoxide and unreacted cyclic imide catalyst;
 (d) contacting at least a portion of the first product with a cleavage catalyst under conditions effective to convert at least part of the cyclohexylbenzene hydroperoxide in said first product into a second product comprising further unreacted cyclic imide catalyst, phenol and cyclohexanone; and
 (e) separating the second product into: (i) a first stream that is rich in at least one of phenol and cyclohexanone; and (ii) a second stream that is rich in further unreacted cyclic imide catalyst.

Conveniently, less than 50 wt %, or less than 30 wt %, or less than 10 wt %, or less than 5 wt %, or less than 1 wt %, of the unreacted cyclic imide catalyst is removed from the first product prior to the contacting step (d), the wt % based upon the weight of the first product.

BRIEF DESCRIPTION OF THE DRAWINGS

FIG. 3 is a graph of cyclohexylbenzene conversion against the batch time in a sulfuric acid-catalyzed cleavage process with NHPI and without NHPI.

FIG. 4 is a graph of phenol yield against batch time in a sulfuric acid-catalyzed cleavage process with NHPI and without NHPI.

FIG. 5 is a graph of phenol yield against batch time in a sulfuric acid-catalyzed cleavage process with NHPI and without NHPI.

DETAILED DESCRIPTION OF THE EMBODIMENTS

Figure 1:
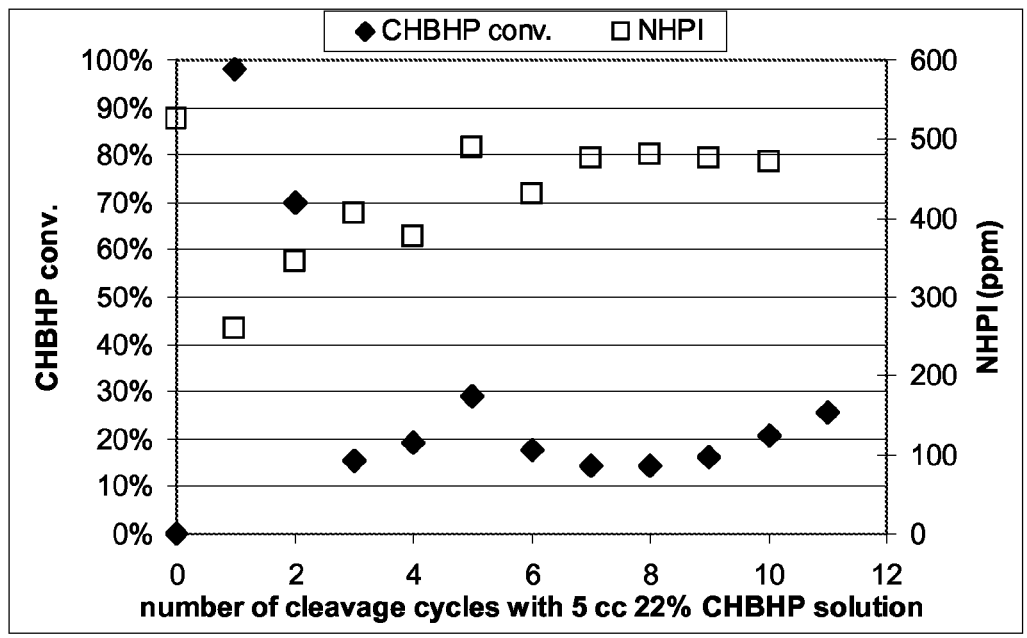
FIG. 1 is a graph of weight % conversion of cyclohexylbenzene hydroperoxide and level of NHPI against number of cleavage cycles in the process of Example 4 using faujasite CBV760 as the cleavage catalyst.

Described herein is a process for producing phenol, in which cyclohexylbenzene is oxidized in the presence of an oxidation catalyst comprising a cyclic imide to produce a first product comprising cyclohexylbenzene hydroperoxide and unreacted cyclic imide catalyst. At least a portion first product is contacted with a cleavage catalyst under conditions effective to convert at least a portion of the cyclohexylbenzene hydroperoxide in said first product into a second product comprising further unreacted cyclic imide catalyst, phenol, and cyclohexanone. The further unreacted cyclic imide catalyst is then removed from the second product and optionally recovered, and/or recycled to the oxidation step.

Conveniently, less than 50 wt %, or less than 30 wt %, or less than 10 wt %, or less than 1 wt %, of the unreacted cyclic imide catalyst is removed from the first product prior to contact with the cleavage catalyst, based upon the weight of the first product.

In one preferred embodiment, the present oxidation and cleavage steps form part of an integrated process for producing phenol and cyclohexanone from benzene, in which the benzene is converted to cyclohexylbenzene, the cyclohexylbenzene is then oxidized to cyclohexylbenzene hydroperoxide and the cyclohexylbenzene hydroperoxide is cleaved to produce phenol and cyclohexanone. The present process will therefore now be more particularly described with reference to this preferred embodiment.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

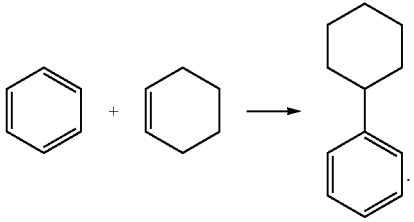 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

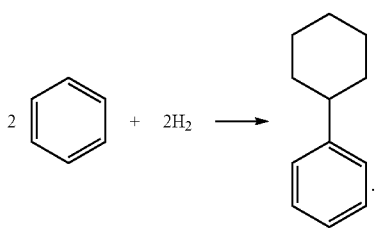 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which, if tiled in three-dimensional space, describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as WO$_x$/ZrO$_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

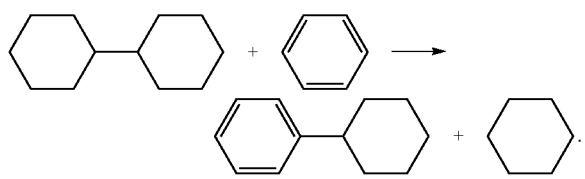

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing compound, such as air and various derivatives of air.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise unreacted imide catalyst and/or unreacted cyclohexylbenzene. As used herein, "unreacted imide catalyst" and "unreacted cyclohexylbenzene" mean that portion of the imide catalyst and cyclohexylbenzene respectively that was not consumed or otherwise transformed in the oxidation reaction. For example, the oxidation reaction effluent may include at least 10 wt %, or at least 20 wt %, or at least 30 wt %, or at least 40 wt %, or at least 50 wt %, or at least 60 wt %, or at least 70 wt %, or at least 80 wt %, or at least 90 wt % of the imide catalyst that is provided to the oxidation reaction. This imide catalyst in the oxidation reaction effluent is referred to as "unreacted imide catalyst." Additionally or alternatively, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In one embodiment, the need for removal of unreacted imide catalyst from the oxidation effluent is obviated, or at least reduced, in the present process by the selection of a cleavage catalyst (e.g., sulfuric acid or acidic molecular sieves, among others).

In one embodiment, less than 1 wt %, or less than 5 wt %, or less than 10 wt %, or less than 20 wt %, or less than 30 wt %, or less than 40 wt %, or less than 50 wt %, or less than 60 wt %, or less than 70 wt %, or less than 80 wt % of the unreacted cyclic imide catalyst is removed from the oxidation effluent prior to the cleavage step, the wt % based upon the weight of the oxidation effluent. In another embodiment, the unreacted cyclic imide catalyst is not deliberately removed from the product prior to the cleavage step. As used herein, "not deliberately removed" means that no steps were undertaken for the purpose of removing the unreacted cyclic imide from the oxidation effluent.

Hydroperoxide Cleavage

Another step in the conversion of the cyclohexylbenzene into phenol and cyclohexanone involves the acid-catalyzed cleavage of the cyclohexyl-1-phenyl-1-hydroperoxide produced in the oxidation step.

Suitable homogeneous cleavage catalysts include, but are not limited to, Brønsted acids and Lewis acids. For example, cleavage catalysts may include sulfuric acid, perchloric acid, phosphoric acid, hydrochloric acid, p-toluene sulfonic acid, trifluoromethyl sulfonic acid, trifluoroacetic acid, aluminum chloride, oleum, sulfur trioxide, ferric chloride, boron trifluoride, sulfur dioxide, and sulfur trioxide.

Other acid catalysts that may be used in the present cleavage reaction include molecular sieves, and in particular molecular sieves having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. Unit cell size is determined by X-ray diffraction as described in ASTM D-3942. As used herein, "FAU-type zeolite" or "zeolite of the FAU type" means a zeolite having a FAU-type structure as described in the *Atlas of Zeolite Framework Types*, Ch. Baerlocher et al. (6th Ed. 2007). The zeolite can be used in unbound form or can be combined with a binder, such as silica or alumina, such that the overall catalyst (zeolite plus binder) comprises from about 20 wt % to about 80 wt % of the zeolite.

In one embodiment, the cleavage catalyst is an acidic molecular sieve which adsorbs at least part of the unreacted cyclic imide catalyst. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

In various embodiments, the oxidation reaction effluent is contacted with a cleavage catalyst under conditions effective to convert a portion of the cyclohexylbenzene hydroperoxide into a cleavage effluent comprising further unreacted cyclic imide catalyst, phenol and cyclohexanone. As used herein, "further unreacted cyclic imide catalyst" means that portion of the unreacted cyclic imide catalyst from the oxidation reaction effluent that was not consumed or transformed in the cleavage reaction.

In one embodiment, at least a portion of the further unreacted cyclic imide catalyst is removed from cleavage effluent. For example, the further unreacted cyclic imide catalyst may be removed from the cleavage effluent through separation into: (i) a first composition that is rich in at least one of phenol and cyclohexanone; and (ii) a second composition that is rich in further unreacted cyclic imide catalyst. Any known or hereinafter devised techniques may be used to effect the separation (e.g., distillation). The further unreacted cyclic imide catalyst may be recovered from the second composition and optionally recycled to the oxidation step. When a stream is described as being "rich in" or "enriched" in a specified species, it is meant that the wt % of the specified species in that stream is enriched relative to the feed stream. For example, where the cleavage effluent is separated into a first composition rich in at least one of phenol and cyclohexanone and a second composition rich in unreacted cyclic imide catalyst, it means that the first composition has a higher wt % than the cleavage effluent of at least one of phenol and cyclohexanone and the second composition has a higher weight percent of unreacted cyclic imide catalyst than the cleavage effluent of unreacted imide catalyst.

In another embodiment, the further unreacted cyclic imide catalyst is removed from the second product through contact with one or more sorbents selected from alkali metal carbonates, alkali metal bicarbonates, alkali metal hydroxides, alkali metal hydroxide-carbonate complexes, alkaline earth metal carbonates, alkaline earth metal bicarbonates, calcium carbonate, ammonium hydroxide, alkaline earth metal hydroxides and alkaline earth metal hydroxide-carbonate complexes, a metal oxide, a hydrogen carbonate, a clay, and an ion exchange resin. The sorbents may also be selected from a group of mixed metal oxides containing Group 2, Group 3, and Group 4 metal oxides. The further unreacted cyclic imide may then be recovered by washing the sorbent with a polar solvent and the further unreacted imide catalyst may optionally be recycled to the oxidation step. Suitable polar solvents include ethanol, acetone, methylethyl ketone, or cyclohexanone. In another embodiment, the further unreacted cyclic imide catalyst is removed from the second product through contact with ammonia or amines (primary, secondary, or tertiary) to form adducts. The further unreacted cyclic imide may then be recovered by treating the adducts with an acid such as acetic acid or hydrochloric acid; and the further unreacted imide catalyst may optionally be recycled to the oxidation step.

In another embodiment, the further unreacted cyclic imide catalyst is removed from the second product through contact with an aqueous solution of a metal carbonate and/or hydrogen carbonate. The further unreacted cyclic imide may be extracted into the aqueous phase and precipitated from the second product, and optionally recovered and recycled to the oxidation step.

In various embodiments, such as when sulfuric acid is used as the cleavage catalyst, the cyclic imide oxidation catalyst may partially decompose during the cleavage process. The decomposed cyclic imide can be disposed as fuel after separation from the cleavage product.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The cleavage reaction can be conducted in a variety of reactor configurations and in either a single reactor or in a plurality of reactors. For example, the reaction may be conducted in at least a first reactor and a second reactor connected in series, with the first reactor being operated at a temperature of about 20° C. to about 120° C. and a pressure of about 100 kPa to about 500 kPa, and the second reactor being operated at a temperature of about 40° C. to about 180° C. and a pressure of about 100 kPa to about 1000 kPa. The first and second reactors may be the same or different.

In one embodiment, at least part of the cleavage reaction is conducted in a continuous stirred tank reactor (CSTR), with the catalyst being slurried in the cleavage reaction medium. Typically, the catalyst is added in an amount between about 50 wppm and about 20,000 wppm of the cleavage reaction medium. Advantages for this configuration include easy heat management and flexibility to add/withdraw catalyst to maintain conversion as the catalyst deactivates. In a slurry cleavage process, the catalyst can be regenerated on various schedules. Advantageously, the catalyst would be continuously withdrawn from the cleavage reactor, regenerated in an external recycle loop, and then returned into the cleavage reactor. Under such operation regime, a steady state of catalyst activity can be maintained through regeneration and by continuously replacing a fraction of the recycled catalyst with fresh catalyst.

When an acidic molecular sieve is employed, (e.g., FAU catalyst) the cleavage reaction can be conducted in a fixed bed plug-flow reactor. In such a process design, two or more parallel cleavage reactor trains may be deployed to enable uninterrupted processing of the peroxide feed. Thus, as the FAU catalyst is saturated with the imide catalyst causing it to deactivate in one reactor train, the cleavage feed is switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In one embodiment, a process for producing phenol comprises:
(a) hydroalkylating benzene with hydrogen in the presence of a hydroalkylation catalyst under conditions effective to produce a hydroalkylation reaction product comprising cyclohexylbenzene;
(b) separating cyclohexylbenzene from said hydroalkylation reaction product;
(c) contacting at least a portion of said cyclohexylbenzene from said separating step (b) with air in the presence of an oxidation catalyst comprising a cyclic imide under oxidation conditions effective to produce a first product comprising cyclohexylbenzene hydroperoxide and unreacted cyclic imide catalyst;
(d) contacting at least a portion of the first product with a cleavage catalyst under conditions effective to convert at least part of the cyclohexylbenzene hydroperoxide in said first product into a second product comprising further unreacted cyclic imide catalyst, phenol and cyclohexanone; and
(e) separating the second product into: (i) a first stream that is rich in at least one of phenol and cyclohexanone; and (ii) a second stream that is rich in further unreacted cyclic imide catalyst.

In various embodiments, less than 1%, or less than 5%, or less than 10%, or less than 20%, or less than 30%, or less than 40%, or less than 50%, or less than 60%, or less than 70%, or less than 80% of the unreacted cyclic imide catalyst is removed from the first product prior to the contacting step (d).

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting examples and the accompanying drawings.

Example 1

Oxidation of cyclohexylbenzene

An amount of 631 g of cyclohexylbenzene (CHB, TCI America, Inc.) was added to a 1-liter four-necked glass flask, to which 0.6702 g of NHPI (TCI America, Inc.) was added. The flask was then fitted with a reflux condenser, a mechanical stirrer, a gas sparger, and a thermometer. An air flow of 250 cc/min was bubbled through the liquid via the gas sparger; and the contents of the flask were heated at 110° C. with stirring (560 rpm) for 6 hours. The flask was allowed to cool down to room temperature and the oxidation product recovered. GC analysis indicated the product contains 17.9% CHBHP. The oxidation product also contained about 1060 ppm of NHPI.

Example 2

Removal of NHPI

An amount of 300 g of the oxidation products from Example 1 was placed in a 500-mL glass flask and mixed with 30 g of anhydrous sodium carbonate (granular form, Aldrich). The mixture was stirred overnight and the solid became brick-red in color. The solid was then removed by filtration and the liquid further filtered through a bed of anhydrous magnesium sulfate. A clear, light-yellow liquid was obtained. GC analysis revealed the product to contain 17.5% CHBHP and <10 ppm NHPI.

Example 3

Cleavage of CHBHP (~3 Wt % CHBHP) Using Faujasite in Batch Operation

An amount of 30 g mixture of CHBHP/CHB/phenol/cyclohexanone (about 3/81/8/8 wt. ratio) and dodecane (internal standard) was charged to a 50-cc jacketed glass reactor with a circulating temperature bath. The bath was set to desired temperature and the reactor contents were allowed to equilibrate. Once the temperature stabilized, a GC sample was taken for the hot feed. The desired amount of a faujasite catalyst commercially available from Zeolyst International under the trade name CBV760 (with a silica to alumina molar ratio of 60 and a unit cell size of 24.24 Å) was then added to the mixture. A brief reaction exotherm was noted, as indicated by the temperature rise inside the reactor, and after a 15 minute interval a 1-cc aliquot was removed from the reactor and the solid filtered. The samples generated were analyzed by GC and the results are summarized in Table 1.

TABLE 1

| Catalyst ($Si/Al_2$) | Catalyst loading | NHPI in feed (ppm) | CHBHP conv. (%) | Phenol selectivity (%) | Cyclohexanone selectivity (%) |
|---|---|---|---|---|---|
| CBV760 | 2% | <10 | 99 | 96 | 93 |
| CBV760 | 2% | ~180 | 99 | 98 | 93 |
| CBV760 | 1% | ~180 | 98 | 98 | 93 |

The results shown in Table 1 demonstrate that the presence of NHPI did not affect the selectivity of the cleavage catalyzed by the faujasite catalyst. As used herein, "CHBHP conversion" means the amount of cyclohexylbenzene hydroperoxide converted to any product. "Phenol selectivity" is relative to the theoretical phenol yield based upon the amount of cyclohexylbenzene hydroperoxide converted. "Cyclohexanone selectivity" is relative to the theoretical cyclohexanone selectivity based upon the amount of cyclohexylbenzene hydroperoxide converted. "Catalyst loading" means the amount of cleavage catalyst per unit amount of the cleavage feed mixture.

Example 4

Concurrent CHBHP Cleavage and NHPI Removal Using Faujasite in a Packed Column A glass column with a stop-cock was packed with glass wool and 10 g of 1 mm glass beads, on top of which was packed 1 g of faujasite powder CBV760, commercially available from Zeolyst International (having a silica to alumina molar ratio of 60 and a unit cell size of 24.24 Å). A volume of 5 cc CHB oxidation mixture containing 22 wt % CHBHP and 550 ppm NHPI (referred as the stock solution) was added to the column and allowed to contact and travel through the bed over a period of 60 min. The liquid was collected; and both the CHBHP the NHPI levels were analyzed. Repeatedly, 5 cc of the stock solution was added and the liquid collected was analyzed. CHBHP conversion and the level of NHPI are plotted against the number of contact cycles in FIG. 1.

The process was repeated but using faujasite powder CBV780, also commercially available from Zeolyst International (having a silica to alumina molar ratio of 80 and a unit cell size of 24.24 Å) as the cleavage catalyst. The results are shown in FIG. 2.

Figure 2:
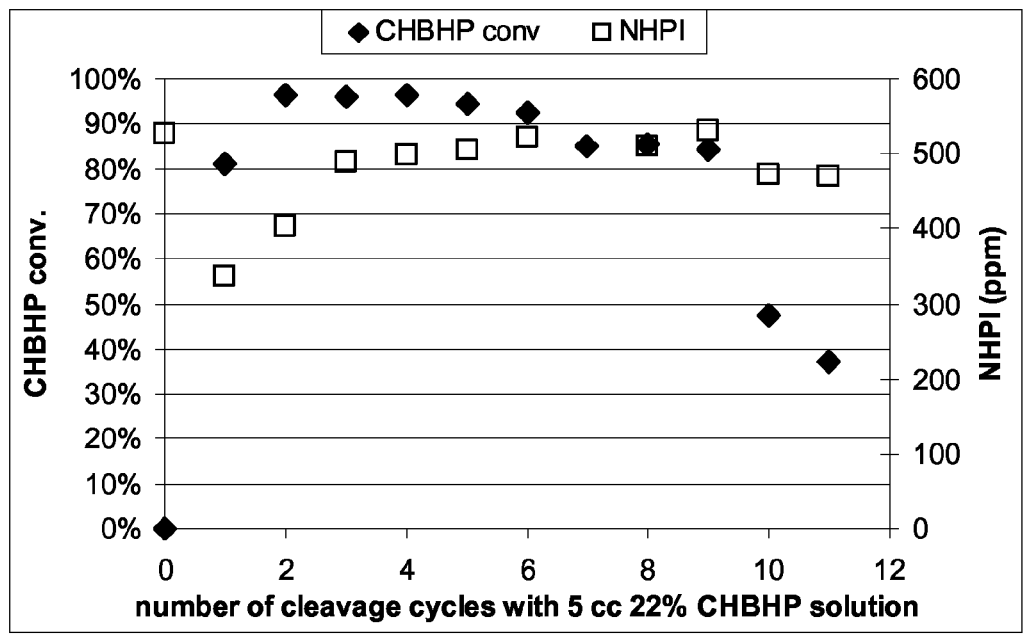
FIG. 2 is a graph of weight % conversion of cyclohexylbenzene hydroperoxide and level of NHPI against number of cleavage cycles in the process of Example 4 using faujasite CBV780 as the cleavage catalyst.

From FIGS. 1 and 2, it can be seen CBV780 showed higher activity for CHBHP cleavage but lower NHPI absorption capacity (0.31 wt %); whereas CBV760 shows higher NHPI absorption capacity (0.63 wt %) but lower activity for CHBHP cleavage.

Example 5

Cleavage of CHBHP (~16 Wt % CHBHP) Using Sulfuric Acid in Batch Operation

The oxidation product generated in Example 1 was used as a NHPI-containing (~1080 ppm) feed for cleavage, while the product from Example 2 was used as feed for comparison where NHPI (<10 ppm) was removed from the cleavage feed.

An amount of 3 g dodecane was mixed with 30 g oxidation product and charged to a 50-cc jacketed glass reactor with a circulating temperature bath. The bath was set to 80° C. and the reactor content was allowed to equilibrate. Once the temperature stabilizes, a GC sample was taken. A desired amount of sulfuric acid (96%, 1000 ppm) was then added to the mixture via a syringe. After a brief reaction exotherm, as indicated by the temperature rise inside the reactor, 1-cc aliquots were taken at certain time intervals and the acid neutralized with 1.5 equivalents of dihexylamine. The samples generated were analyzed by GC.

From FIGS. 3-5, it can be seen that the presence of NHPI did not affect conversion or yield in sulfuric acid-catalyzed cleavage.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) contacting cyclohexylbenzene with an oxygen-containing compound in the presence of an oxidation catalyst comprising a cyclic imide under oxidation conditions effective to produce a first product comprising cyclohexylbenzene hydroperoxide and unreacted cyclic imide catalyst;
   (b) contacting at least a portion of the first product with a cleavage catalyst under conditions effective to convert at least a portion of the cyclohexylbenzene hydroperoxide in said first product into a second product comprising further unreacted cyclic imide catalyst, phenol and cyclohexanone, wherein less than 50 wt % of the unreacted cyclic imide catalyst is removed from the first product prior to the contacting step (b); and
   (c) removing at least a portion of the further unreacted cyclic imide catalyst from the second product.

2. The process of claim 1, wherein less than 10 wt % of the unreacted cyclic imide catalyst is removed from the first product prior to the contacting step (b).

3. The process of claim 1, wherein less than 1 wt % of the unreacted cyclic imide catalyst is removed from the first product prior to the contacting step (b).

4. The process of claim 1, wherein the removing step (c) comprises separating the second product into (i) a first composition that is rich in at least one of phenol and cyclohexanone; and (ii) a second composition that is rich in further unreacted cyclic imide catalyst.

5. The process of claim 4, further comprising recovering at least a portion of the further unreacted cyclic imide catalyst from the second composition and recycling at least a portion of the recovered further unreacted cyclic imide catalyst to the contacting step (a).

6. The process of claim 1, wherein the cleavage catalyst is selected from sulfuric acid, perchloric acid, phosphoric acid, hydrochloric acid, p-toluene sulfonic acid, trifluromethyl sulfonic acid, trifluroacetic acid, aluminum chloride, oleum, sulfur trioxide, ferric chloride, boron trifluoride, sulfur dioxide and sulfur trioxide, and acidic molecular sieves.

7. The process of claim 1, wherein the cleavage catalyst is selected from sulfuric acid and an acidic molecular sieve.

8. The process of claim 1, wherein the cyclic imide catalyst is N-hydroxyphthalimide.

9. The process of claim 1, wherein the further unreacted cyclic imide catalyst is removed from the second product through contact with one or more sorbents selected from alkali metal carbonates, alkali metal bicarbonates, alkali metal hydroxides, alkali metal hydroxide-carbonate complexes, alkaline earth metal carbonates, alkaline earth metal bicarbonates, calcium carbonate, ammonium hydroxide, alkaline earth metal hydroxides and alkaline earth metal hydroxide-carbonate complexes, a metal oxide, a hydrogen carbonate, a clay and an ion exchange resin, mixed metal oxides containing Group 2, Group 3, and Group 4 metal oxides.

10. The process of claim 9, wherein the further unreacted cyclic imide is recovered from the one or more sorbents by washing the one or more sorbents with a polar solvent.

11. The process of claim 10, wherein the polar solvent is one or more of ethanol, acetone, methylethyl ketone and cyclohexanone.

12. The process of claim 1, wherein the further unreacted cyclic imide catalyst is removed from the second product through contact with ammonia, primary amines, secondary amines, tertiary amines, and mixtures thereof.

13. The process of claim 12, wherein the further unreacted cyclic imide is recovered from the adducts with ammonia or amines by contact with an acid.

14. The process of claim 13, wherein the acid is acetic acid or hydrochloric acid.

15. The process of claim 10, wherein at least a portion of the recovered further unreacted imide catalyst is recycled to the contacting step (a).

16. The process of claim 13, wherein at least a portion of the recovered further unreacted imide catalyst is recycled to the contacting step (a).

17. The process of claim 1, wherein the further unreacted cyclic imide catalyst is removed from the second product through contact with an aqueous solution of a metal carbonate and/or hydrogen carbonate.

18. The process of claim 17, wherein removing the further unreacted cyclic imide catalyst from the second product comprises extracting the further unreacted cyclic imide catalyst into the aqueous phase and precipitating the further unreacted cyclic imide catalyst from the second product by treatment with one or more acids selected from acetic acid or hydrochloric acid.

19. The process of claim 18, further comprising recovering the precipitated further unreacted imide catalyst and recycling the further unreacted cyclic imide catalyst to the contacting step (a).

20. The process of claim 1, wherein the cleavage catalyst is an acidic molecular sieve and the conditions in the contacting step (b) are effective to adsorb at least part of the unreacted cyclic imide catalyst.

21. The process of claim 1, wherein said conditions in the contacting step (b) include a temperature of about 20° C. to about 200° C. and a pressure of about 100 kPa to about 2000 kPa.

22. A process for producing phenol, the process comprising:
(a) hydroalkylating benzene with hydrogen in the presence of a hydroalkylation catalyst under conditions effective to produce a hydroalkylation reaction product comprising cyclohexylbenzene;
(b) separating cyclohexylbenzene from said hydroalkylation reaction product;
(c) contacting at least a portion of said cyclohexylbenzene from said separating step (b) with air in the presence of an oxidation catalyst comprising a cyclic imide under oxidation conditions effective to produce a first product comprising cyclohexylbenzene hydroperoxide and unreacted cyclic imide catalyst;
(d) contacting at least a portion of the first product with a cleavage catalyst under conditions effective to convert at least part of the cyclohexylbenzene hydroperoxide in said first product into a second product comprising further unreacted cyclic imide catalyst, phenol, and cyclohexanone; and
(e) separating the second product into: (i) a first stream that is rich in at least one of phenol and cyclohexanone; and (ii) a second stream that is rich in further unreacted cyclic imide catalyst.

* * * * *